United States Patent [19]

Sancoff

[11] Patent Number: 5,308,334
[45] Date of Patent: May 3, 1994

[54] CLOSED SYSTEM FOR IV SITE FLUSH

[75] Inventor: Gregory E. Sancoff, Leucadia, Calif.

[73] Assignee: Block Medical, Inc., Carlsbad, Calif.

[21] Appl. No.: 842,443

[22] Filed: Feb. 27, 1992

Related U.S. Application Data

[63] Continuation of Ser. No. 634,408, Dec. 27, 1990, abandoned.

[51] Int. Cl.⁵ .............................................. A61M 37/00
[52] U.S. Cl. ..................................... 604/131; 604/82;
  604/83; 604/181; 604/410; 222/95; 222/97;
  222/103
[58] Field of Search ................. 604/71, 80, 82, 83,
  604/85, 89, 90, 118, 131, 132, 134, 142, 151,
  153, 181-185, 257-259, 262, 410; 222/93, 94,
  95, 97, 101-104

[56] References Cited

U.S. PATENT DOCUMENTS

| 1,102,953 | 7/1914 | Rabat | 604/134 |
|---|---|---|---|
| 1,546,016 | 7/1925 | Eisele | 604/262 |
| 3,194,440 | 7/1965 | Watson, Jr. | 222/103 |
| 3,442,424 | 5/1969 | Prussin et al. | 604/200 |
| 3,595,232 | 7/1971 | Leibinsohn | 604/134 |
| 3,734,351 | 5/1973 | Gaudin | 604/134 |
| 3,780,730 | 12/1973 | Leibinsohn | 604/134 |
| 4,044,757 | 8/1977 | McWhorter et al. | 604/82 |
| 4,187,845 | 2/1980 | Dror | 604/182 |
| 4,504,267 | 3/1985 | Parmelee et al. | 604/134 |
| 4,512,764 | 4/1985 | Wunsch | 604/83 |
| 4,576,603 | 3/1986 | Moss | 604/410 |
| 4,666,430 | 5/1987 | Brown et al. | 604/141 |
| 4,753,371 | 6/1988 | Michielin et al. | 222/94 |
| 4,830,510 | 5/1989 | Bellhouse | 604/416 |
| 4,857,055 | 8/1989 | Wang | 604/133 |
| 4,915,688 | 4/1990 | Bischof et al. | 604/83 |
| 4,957,436 | 9/1990 | Ryder | 222/94 |
| 4,997,083 | 3/1991 | Loretti et al. | 604/410 |

FOREIGN PATENT DOCUMENTS

| 1013635 | 7/1977 | Canada | 604/134 |
|---|---|---|---|
| 3238649 | 4/1984 | Fed. Rep. of Germany | 604/131 |
| 2570279 | 3/1986 | France | 604/410 |

Primary Examiner—C. Fred Rosenbaum
Assistant Examiner—Ronald Stright, Jr.
Attorney, Agent, or Firm—Baker, Maxham, Jester

[57] ABSTRACT

A closed system for flushing an IV site comprises a unitary reservoir assembly of a first fluid reservoir for containing a first flush fluid, a second fluid reservoir for containing a second flush fluid, a tubing array for connecting the first and the second reservoirs to an IV site comprising a common tube having a connector on one end thereof for connection to the site, and mounted in a housing having depressible panels for selectively controlling the flow of a fluid from each of the first and the second reservoirs.

19 Claims, 2 Drawing Sheets

CLOSED SYSTEM FOR IV SITE FLUSH

REFERENCE TO RELATED APPLICATION

This is a continuation of application Ser. No. 07/634,408, filed Dec. 27, 1990, entitled "Closed System For IV Site Flush" now abandoned.

BACKGROUND OF THE INVENTION

The present invention relates to an IV drug delivery apparatus and pertains particularly to an improved IV site flush system.

Because of the high cost of administering health care in this country, many patients administer their own intravenous therapy (IV) at home. Many times, such therapy requires the periodic infusion of one or more therapeutic fluids, such as an antibiotic. The patient is usually equipped with an IV tubing set, typically called an IV infusion site or IV site when installed. The IV site typically consists of a needle or catheter inserted into a vein of the patient by trained medical personnel and attached to a tubing set which is strapped or taped to the patient to enable easy attachment of an infuser device. The tubing set is equipped with an injection port or cap into which a needle is inserted to administer or infuse the therapeutic fluid. It may also have other forms of coupling, such as a luer lock coupling.

Between infusions, blood may coagulate and clog the IV needle and/or tubing. In order to overcome this problem, an anticoagulant such as heparin is introduced into the IV site after an infusion. A preferred procedure is to flush the IV site with a saline solution before and after the infusion, and fill or flush the IV site with heparin after the second saline flush.

Currently in the health care industry, IV sites are flushed with a saline solution before infusion and after the infusion is complete. A heparin solution is then injected into the site to prevent coagulation between infusion periods. This is carried out by means of a separate syringe and hypodermic needle for each saline flush. The catheter and needle area of the vein are then filled with the heparin by means of another syringe after the infusion and second saline flush.

This procedure is carried out with at least three syringes, three 25G needles, and vials of saline and heparin. The patient or nurse draws fluid into the syringe and pierces the injection port of the IV site to inject for each stage of the procedure. The IV site is pierced first for saline, second for the IV therapy, third for saline and fourth for heparin. This requires the use and disposal of at least three syringes and four needles with each treatment, and increases the risk of mistake or contamination due to the many open instruments and connections.

The present invention provides a closed system wherein the syringes and multiple needles are eliminated, and the IV site is pierced only once for each treatment.

SUMMARY AND OBJECTS OF THE INVENTION

It is the primary object of the present invention to provide an improved IV site flush system.

In accordance with a primary aspect of the present invention, an IV site flush system comprises a closed self-contained system having a plurality of solution reservoirs, usually a saline reservoir and a heparin reservoir with a common connection to an IV site.

BRIEF DESCRIPTION OF THE DRAWING

The above and other objects and advantages of the present invention will become apparent from the following description when read in conjunction with the accompanying drawings wherein.

DETAILED DESCRIPTION OF A PREFERRED EMBODIMENT

Figure 1:
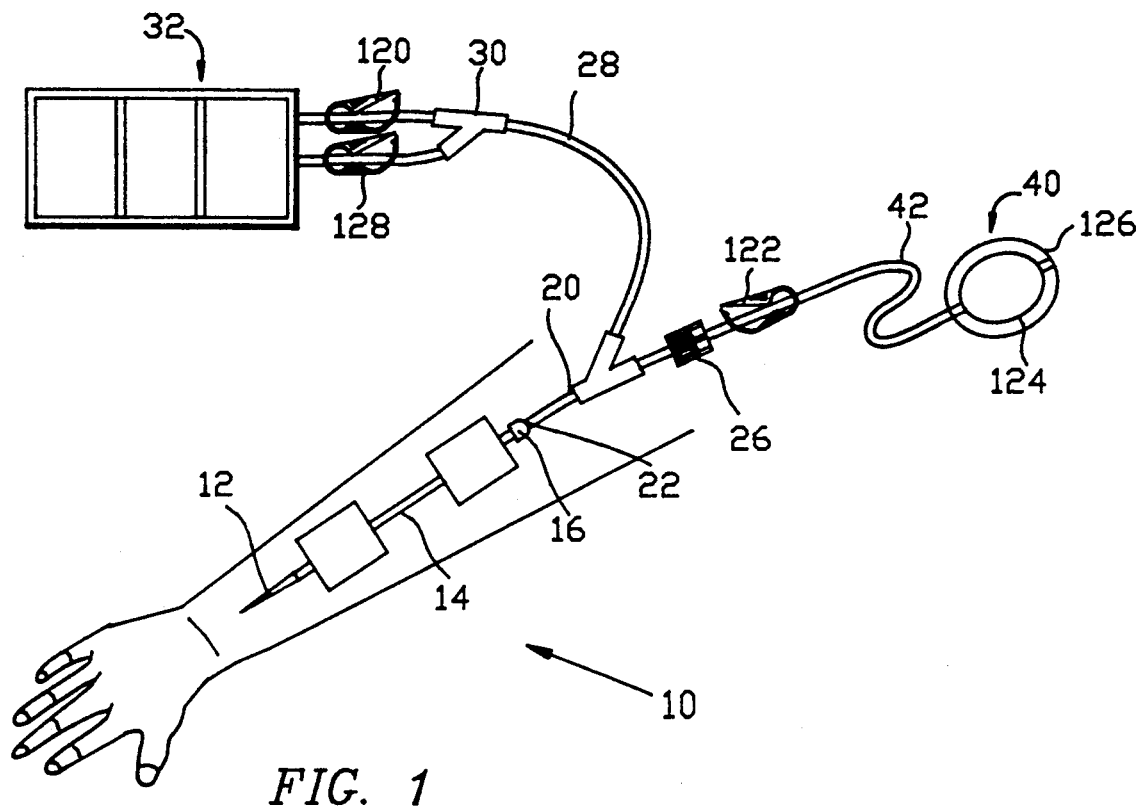
FIG. 1 is a perspective view illustrating a preferred embodiment of the invention in operation.

Referring to the drawing, and particularly to FIG. 1, there is illustrated a typical IV infusion or injection site to which is attached a combination of an infusion device 40 and a flush system 32 in accordance with the invention. A typical IV infusion site (typically called IV site), as illustrated, comprises an IV needle 12 inserted in a vein of a patient's arm, with a short catheter or length of tubing 14 connected thereto and having a connector 16, such as an infusion port or cap on an outer end thereof for connection of an infusion pump or device. The IV site needle and catheter unit are typically held in place by one or more strips of tape or the like 13 and 15, and may include one or more protective covers (not shown). The connector 16 may be of the type for penetrating by a needle or the like, or it may be of the luer lock type for detachable connection to an infuser.

In the illustrated embodiment, a flush system in accordance with the invention comprises a reservoir assembly having an integral tubing array for connection to an IV site. The tubing array comprises a first section of tubing 20 having a first or proximal end 22 for connection to the catheter 14, and a Y coupling 24 including a coupling 26 for connection of an infusion device, and a tubing 28 having a Y coupling 30 connected to the flush system reservoirs 34 and 36.

Figure 2:
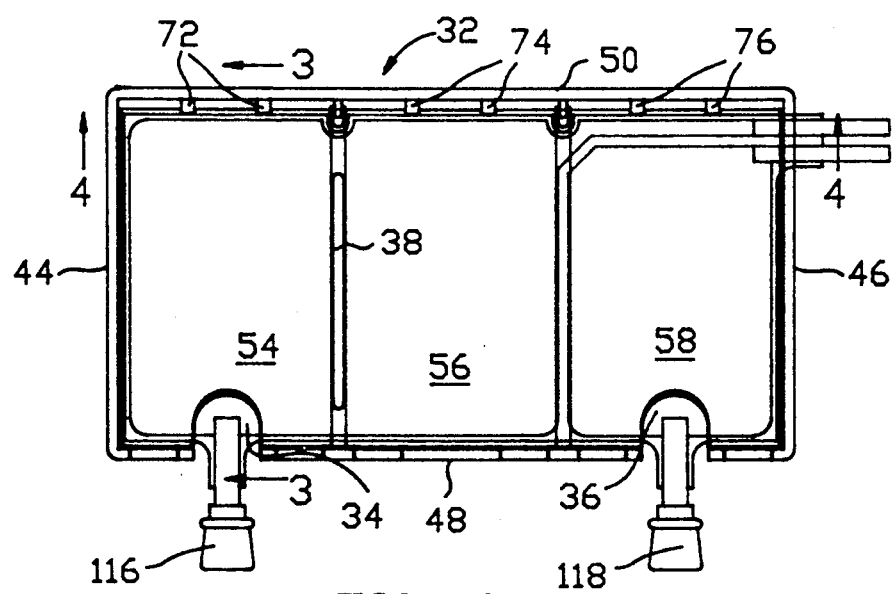
FIG. 2 is a top plan view of the embodiment of FIG. 1.

The reservoir assembly, as best seen in FIG. 2, is a unitary structure of impervious pliable material formed into two reservoirs 34 and 36. The reservoir assembly is illustrated in FIG. 2 in a transparent housing. The overall reservoir is a generally rectangular pliable bag, with the walls sealed together along a line 35 to form reservoirs 34 and 36. The reservoir 34 is separated along a line 38 into two connected chambers. The reservoir 34 with its two chambers is designed for two saline charges of about 3 ml each, and the reservoir 36 is designed for a heparin charge of about 3 ml.

These reservoirs are preferably of a pliable impervious material, such as PVC, typically used for IV bags and the like. The two chambers of reservoir 34 are permanently connected via a tube 37 to a Y coupling 30 and common tube 28. The reservoir 36 is likewise permanently connected via tube 39 to Y coupling 30 and common tube 28. The system is a closed system capable of performing its functions with a one time connection. The system requires only a single one time connection at 16, 22 for connecting three charges of fluid to the IV site. The infusion device 40 can be connected to the IV site at 26 at the same time that the flush system is connected.

Any suitable IV infusion device 40, such as for example of the type disclosed in co-pending application Ser. No. 07/492,982, filed Mar. 12, 1990, now U S. Pat. No. 5,080,652, granted Jan. 14, 1992, and assigned to the assignee hereof, is connected by a usual tubing or line 42 to the infusion coupling 26. This coupling is by suitable means, such as a needle cap or a luer lock. The flush system may be utilized with any suitable infuser.

Figure 3:
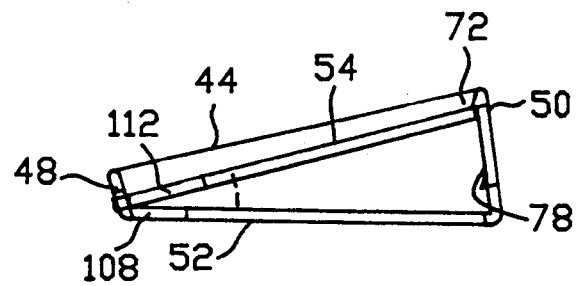
FIG. 3 is a side elevation view in section taken generally on line 3—3 of FIG. 2.

Referring to FIG. 2, the housing 32 of the flushing device 32 is preferably of a generally rectangular configuration in top or plan view, and of a generally triangular cross section configuration in side view (FIG. 3). The housing is preferably constructed of a transparent rigid plastic. As seen in FIGS. 2 and 3, the housing has triangular end walls 44 and 46, and generally rectangular front and back walls 48 and 50 extending upward from a generally planar rectangular bottom wall 52, forming a generally triangular, or more particularly wedge shaped cavity or chamber in which the reservoirs 34 and 36 are disposed. A top wall is formed of multiple panels or sections 54, 56 and 58. The panels or sections 54 and 56 overlie and are co-planar with the two chambers of saline reservoir 34, and the panel 58 is co-planar with the heparin reservoir 36. These panels are each hingedly or pivotally secured along the front to the lower edge of the front wall 48 by suitable tabs and slots. The back edge of each panel engages latching wedges on the inside top and bottom of the back wall 50.

Figure 4:
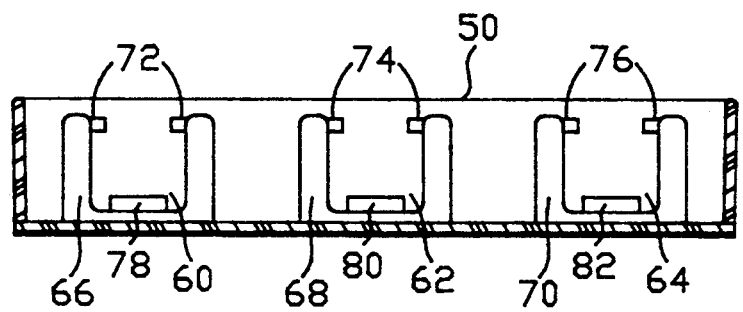
FIG. 4 is an elevation view taken generally on line 4—4 of FIG. 2.

Referring to FIGS. 3 and 4, the back wall 50 is formed of three spring panels 60, 62, and 64 by U-shaped slots 66, 68 and 70. Each of the spring panels are provided with a pair of upper wedge shaped latch shoulders 72, 74 and 76 for latching the upper or top wall panels 54, 56 and 58 in an initial assembled position, as seen in FIG. 3. A lower latch shoulder 78, 80 and 82 is provided at the lower edge of each panel to latch the top wall panels in the collapsed position. Intermediate latch notches may be provided (i.e. between 72 and 78), refer to FIG. 6, so that each reservoir may have multiple charges.

Figure 5:
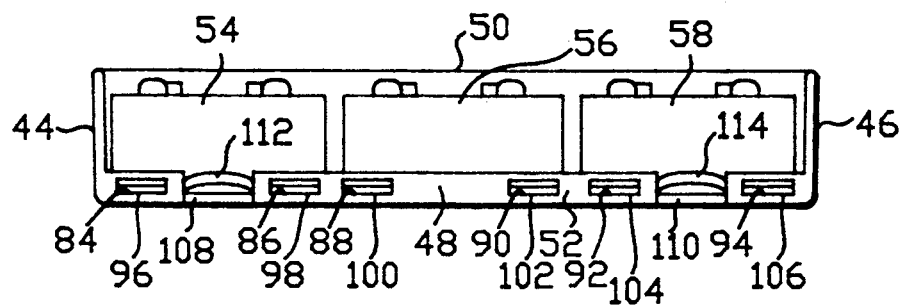
FIG. 5 is a front elevation view of the housing of the embodiment of FIG. 1.

Referring to FIGS. 3 and 5, the front wall 48 is provided with a plurality of rectangular slots 84, 86, 88, 90, 92 and 94. Each of the top wall panels is provided with a pair of tabs 96, 98, 100, 102, 104 and 106 which extend into the slots for hinging the respective panels in the housing. A pair of slots 108 and 110 in the front wall 48 and bottom 52, and matching slots 112 and 114 in top panels 54 and 58 provide a pair of openings through which filler ports 116 and 118 for bladder reservoirs 34 and 36 extend.

The housing is thus constructed to have collapsible top walls, such that the sections of the wall can be selectively collapsed against the reservoirs, forcing a liquid therefrom. As illustrated in FIGS. 3 and 4, each of the top wall panels 54, 56 and 58 may be pressed downward by the fingers or other suitable means, such as a spring to latch in a position closely adjacent the lower wall of the housing, thereby forcing the liquid from the respective reservoirs. Thus, the walls 54, 56 and 58 may be selectively pushed downward, expelling a charge of the fluid from the space beneath the respective panel, and latched in a lower position to effectively force a selected portion or all of the liquid from the respective reservoir or portion thereof.

The reservoir 34, in the illustrated embodiment, is designed to hold two charges (in adjacent portion of the reservoir), with panels or walls 54 and 56 effective in sequence to respectfully discharge these charges. In other words, the first panel pressed down, preferably 54, expels half of the contents or charge and the second panel expels the remainder. However, each panel may be effective to expel two or more charges, as explained above. It will also be appreciated that other means, such as rollers or merely opposed panels, may be utilized to collapse the walls of the reservoirs and expel fluid therefrom. The reservoirs are each provided with suitable valves, which may be built into the housing (not shown) or such as clamps 120 and 128.

Figure 6:
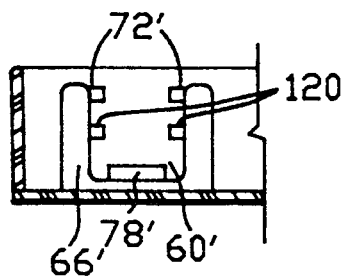
FIG. 6 is a partial detailed view in section like FIG. 4 illustrating an alternate modification.

Referring to FIG. 6, an alternate modification is illustrated wherein like elements are identified by like numbers primed. In this embodiment, the back wall is modified to provide latch bumps or shoulders 130 intermediate the latch shoulders 72' and 78' on the spring latch panel 60'. Thus, multiple charges are provided as above described for each reservoir or chamber of a reservoir. The reservoirs of the system are designed to hold about three (3) ml charges for flushing.

In normal operation, a flush kit in accordance with the invention is factory assembled, with a pair of reservoirs 34 and 36 placed in the housing, with tube assembly 20, 22, 28 and 30 attached thereto. The top panels 54, 56 and 58 are put in place by inserting the tabs into the slots and pressing the panel down, so that the back edge snaps over the top shoulder wedges 72, 74 and 76 When ready for use, they are filled by a pharmacist via fill ports 116 and 118 and delivered to a health care official or patient for use in IV therapy.

In the usual procedure, an IV site is or has been installed by medical or health care personnel and left in place for successive IV treatment. The patient selects a fresh filled flush kit, and the end 22 of tubing 20 is connected at cap 16 to the IV site. If infusion therapy is to be administered, an infuser 40 is attached at coupling 26 to the flush kit. The IV site is first flushed by opening a valve or clamp 120 on the saline feeding tube, and then pressing down on panel 54 with the fingers until the fluid is expelled, and the panel is latched beneath the lower latch notch 78. The clamp 120 is then reclosed and infusion may begin by releasing a clamp 122 on an infusion apparatus tubing 42 to feed the IV solution from an infuser or infusion apparatus 40.

The infuser may be of any suitable type, but is preferably of the inflatable bladder type having an inflatable bladder within a housing. One preferred type is that of the aforementioned application wherein the inflatable bladder 124 is mounted within a substantially or generally spherical housing or shell 126. The term substantially or generally spherical is not intended to connote spherical with mathematical precision, but is intended to allow variation within practical limits.

After the infusion is complete, the site is again flushed with a saline solution (about 3 ml) by again opening clamp 120, and then depressing the second panel 56 until remaining fluid is expelled, and the panel 56 is latched beneath the latch notch or tab 80, and the saline reservoir is thus empty. The clamp 120 is then reapplied to the tubing, and clamp 128 from the heparin reservoir 36 is then opened. The panel 58 is then depressed with the fingers until the heparin has been forced from the reservoir, the panel latched beneath latch notch 82, and the heparin has been forced into the IV site. The flush unit may now be removed from the cap 16, and it together with the infusion apparatus disposed of in the usual manner.

The present system was devised primarily for use as a flush system, as described above. However, it may have many other uses, such as infusion of micro doses of different drugs sequentially. The system may also be constructed to have any number of reservoirs and/or chambers.

While I have illustrated and described my invention by means of specific embodiments, it should be understood that numerous changes and modifications may be made therein without departing from the spirit and scope of the invention as defined in the appended claims.

I claim:

1. A closed system for flushing an IV infusion site comprising:
   a box-like housing having a chamber;
   a unitary pliable reservoir assembly disposed in said chamber and comprising a first fluid reservoir for containing a first flush fluid, a second fluid reservoir for containing a second flush fluid, said first and said second reservoirs are disposed in side by side relation and one of said reservoirs is divided into two interconnected chambers;
   a tubing array connecting said first and said second reservoirs together and for connecting to an IV infusion site comprising a common tube having means on one end thereof for connection to said site, and means on the other end thereof for controlling communication of each of said first and said second reservoirs via said common tube to said site; and
   means for selectively positively collapsing each of said first and said second reservoirs for controlling the flow of a fluid therefrom.

2. A closed system according to claim 1 wherein said common tube has coupling means for coupling an IV infusion device thereto.

3. A closed system according to claim 2 wherein said means for selectively positively collapsing each of said first and said second reservoirs comprises separate pivoting wall means for collapsing each of said reservoirs.

4. A closed system according to claim 3 wherein:
   said housing has a triangular shape in cross section; and
   means for latching said pivoting walls in a collapsed position.

5. A closed system according to claim 1 wherein said means for collapsing said reservoirs comprises pivoting wall means contacting said reservoirs and responsive to pressure for biasing said reservoirs to a collapsed condition.

6. A closed system according to claim 5 wherein:
   said housing has a triangular shape in cross section; and
   means for latching said pivoting walls in a selected one of a partially collapsed and a fully collapsed position.

7. A closed system according to claim 1 further comprising:
   an infusion device comprising a generally spherical shell;
   an inflatable bladder in said spherical shell; and
   tubing means connected to said bladder and to said tubing array for conveying a fluid in said bladder to the IV infusion site.

8. A closed system for flushing an IV site comprising:
   a box-like housing having a chamber;
   a unitary pliable reservoir assembly disposed in said chamber and comprising a first fluid reservoir for containing a first flush fluid, a second fluid reservoir for containing a second flush fluid;
   a tubing array connecting said first and second reservoirs together and for connecting to an IV infusion site comprising a common tube having means on one end thereof for connection to said site, and means on the other end thereof for controlling communication of each of said first and said second reservoirs via said common tube to said site; and
   means for selectively positively collapsing each of said first and second reservoirs for controlling the flow of a fluid therefrom wherein said means for collapsing said reservoir comprises separate pivoting wall means contacting each of said reservoirs and responsive to pressure for biasing said reservoirs to a collapsed condition.

9. A closed system according to claim 8, wherein:
   said first and said second reservoirs are disposed in side by side relation and one of said reservoirs is divided into two interconnected chambers, and said housing has a triangular shape in cross section; and
   further comprising means for latching said pivoting walls in a collapsed position.

10. A closed system according to claim 9 wherein:
    said housing has a triangular shape in cross section.

11. A closed system according to claim 8 wherein:
    said housing has a triangular shape in cross section; and
    means for latching said pivoting walls in a collapsed position.

12. A closed system according to claim 8 wherein said common tube includes coupling for coupling an IV infuser thereto.

13. A closed system according to claim 8 further comprising:
    an infusion device comprising a generally spherical shell;
    an inflatable bladder in said spherical shell; and
    tubing means connected to said bladder and to said tubing array for conveying a fluid in said bladder to the IV infusion site.

14. A closed IV site flushing system for flushing an IV infusion site with multiple fluids comprising in combination:
    a housing having walls defining a wedge shaped chamber;
    a unitary reservoir construction comprising a first pliable fluid reservoir having first and second fluid chambers for containing separate charges of a first flush fluid, and a second pliable fluid reservoir for containing a second flush fluid disposed in said housing;
    a tubing array connected to said first and said second fluid reservoirs and having connecting means on an end thereof for connecting to an IV infusion site; and
    housing means for selectively engaging and separately collapsing said first and said second reservoirs for controlling the flow of a fluid from each of said first and said second reservoirs to said infusion site.

15. A closed system according to claim 14 wherein said tubing array has coupling means for coupling an IV infusion device thereto.

16. A closed system according to claim 15 wherein said housing means for collapsing said reservoirs comprises pivoting wall means contacting said reservoirs and responsive to pressure for biasing said reservoirs to a selected collapsed condition.

17. A closed system according to claim 16 wherein:
said housing has a triangular shape in cross section; and
means for latching said pivoting walls in a selected one of a partially and a fully collapsed position.

18. A closed system according to claim 14 further comprising:
an infusion device comprising a generally spherical shell;
an inflatable bladder in said spherical shell; and
tubing means connected to said bladder and to said tubing array for conveying a fluid in said bladder to the IV infusion site.

19. A closed system according to claim 18 wherein said housing means for collapsing said reservoirs comprises pivoting wall means contacting said reservoirs and responsive to pressure for biasing said reservoirs to a collapsed condition.

* * * * *